US010441626B2

(12) United States Patent
Schwach et al.

(10) Patent No.: US 10,441,626 B2
(45) Date of Patent: Oct. 15, 2019

(54) MICROPARTICLES COMPRISING GNRH MADE BY PGSS

(71) Applicant: Ferring B.V., Hoofddorp (NL)

(72) Inventors: Gregoire Charles Joseph Schwach, Copenhagen (DK); Lars Schiefelbein, Basel (CH); Andrew Naylor, Nottingham (GB); Mark Andrew Whitaker, Nottingham (GB); Nicholas John Arrowsmith, Nottingham (GB)

(73) Assignee: Ferring BV, Hoofddorp (NL)

( * ) Notice: Subject to any disclaimer, the term of this patent is extended or adjusted under 35 U.S.C. 154(b) by 0 days.

(21) Appl. No.: 15/027,754

(22) PCT Filed: Oct. 7, 2014

(86) PCT No.: PCT/EP2014/071474
§ 371 (c)(1),
(2) Date: Apr. 7, 2016

(87) PCT Pub. No.: WO2015/052204
PCT Pub. Date: Apr. 16, 2015

(65) Prior Publication Data
US 2016/0228494 A1 Aug. 11, 2016

(30) Foreign Application Priority Data
Oct. 8, 2013 (EP) .................................. 13187665

(51) Int. Cl.
*A61K 38/09* (2006.01)
*A61K 9/16* (2006.01)
*A61K 38/22* (2006.01)

(52) U.S. Cl.
CPC ............ *A61K 38/09* (2013.01); *A61K 9/1647* (2013.01); *A61K 38/22* (2013.01)

(58) Field of Classification Search
CPC ....... A61K 38/09; A61K 38/22; A61K 9/1647
See application file for complete search history.

(56) References Cited

U.S. PATENT DOCUMENTS 5,134,122 A * 7/1992 Orsolini ............... A61K 9/0024
424/489
5,744,153 A * 4/1998 Yewey ................. A61K 9/0024
424/426
(Continued)

FOREIGN PATENT DOCUMENTS

| DE | 40 23 134 A1 | 1/1991 | |
| JP | 03-066625 | 3/1991 | |
| JP | 2011-527328 | 10/2011 | |
| WO | WO 2006/01055 A2 | 1/2006 | |
| WO | WO 2006010155 A2 * | 1/2006 | ........... A61K 9/0019 |
| WO | WO-2006010155 A2 * | 1/2006 | ........... A61K 9/0019 |

(Continued)

OTHER PUBLICATIONS

Rodrigues et al. (Microcomposites theophylline/hydrogenated palm oil from a PGSS process for controlled drug delivery systems, 2004).*

(Continued)

*Primary Examiner* — Aradhana Sasan
*Assistant Examiner* — Quanglong N Truong
(74) *Attorney, Agent, or Firm* — Finnegan, Henderson, Farabow, Garrett & Dunner, LLP

(57) ABSTRACT

A pharmaceutical formulation comprising a solid matrix of one or more biodegradable polymers, the solid matrix including a pharmaceutically active substance or a pharmaceutically acceptable salt thereof distributed homogeneously or substantially homogeneously within the matrix; wherein the pharmaceutically active substance is, for example, a gonadotropin releasing hormone (GnRH), a GnRH agonist or a GnRH antagonist.

27 Claims, 5 Drawing Sheets

(56) References Cited

U.S. PATENT DOCUMENTS

| | | | |
|---|---|---|---|
| 2002/0130430 A1 | 9/2002 | Castor | |
| 2006/0074027 A1* | 4/2006 | Saito | A61K 9/5031 424/468 |
| 2007/0275082 A1 | 11/2007 | Lee et al. | |
| 2011/0172141 A1* | 7/2011 | Naylor | A61K 9/1647 514/1.1 |

FOREIGN PATENT DOCUMENTS

| | | | | |
|---|---|---|---|---|
| WO | WO 2010/004287 | | 1/2010 | |
| WO | WO 2012/013331 A2 | | 2/2012 | |
| WO | WO 2012013331 A2 * | | 2/2012 | A61K 9/4808 |
| WO | WO-2012013331 A2 * | | 2/2012 | A61K 9/4808 |

OTHER PUBLICATIONS

Mishima, Kenki, "Biodegradable particle formation for drug and gene delivery using supercritical fluid and dense gas", Advanced Drug Delivery Reviews, vol. 60, No. 3, pp. 411-432 (2007).

Rodrigues, M., et al., "Microcomposites theophyliine/hydrogenated palm oil from a PGSS process for controlled drug delivery systems", Journal of Supercritical Fluids, vol. 29, No. 1-2, pp. 175-184 (2004).

De Paz, E., et al., "Formulation of β-carotene with poly-(-caprolactones) by PGSS process", Powder Technology, vol. 217, pp. 77-83 (2011).

Schwach G., et al., "Biodegradable microparticles for sustained release of a new GnRH antagonist—part I: screening commercial PLGA and formulation technologies", European Journal of Pharmaceutics and Biopharmaceutics, vol. 56, No. 3, pp. 327-336 (2003).

PCT International Search Report, PCT/EP2014/071474, dated Dec. 15, 2014.

Pignatello, R., "PLGA-alendronate conjugate as a new biomaterial to produce osteotropic drug nanocarriers," Biomaterials Applications for Nanomedicine, pp. 165-184, Nov. 2011.

Schwach G. et al: "Biodegradable microparlicles for sustained release of a new GnRH antagonist-part I: screening commercial PLGA and formulation technologies", European Journal of Pharmaceutics and Biopharmaceutics, Elsevier Science Publishers B.V., Amsterdam, NL, vol. 56, No. 3, Nov. 1, 2003, pp. 327-336.

* cited by examiner

MICROPARTICLES COMPRISING GNRH MADE BY PGSS

This is a national stage application under 35 U.S.C. § 371 of International Application No. PCT/EP2014/071474, filed Oct. 7, 2014, and claims priority to European Patent Application No. 13187665.8, filed Oct. 8, 2013, the content of each of which is incorporated herein by reference.

The present invention relates to formulations for sustained, extended, and/or delayed (or otherwise controlled) release of a pharmaceutically active substance such as a peptide. The formulations may be for use in the treatment of disease, for example the formulations may be used for the treatment and/or prevention of prostate cancer.

Prostate cancer is a leading cause of mortality and morbidity for men in the industrialized world. The majority of prostate cancers are dependent on testosterone for growth, and the current medical approach in the management of advanced prostate cancer involves androgen deprivation. The aim is to reduce serum testosterone (T) to below castrate level (T≤0.5 ng/mL). This may be achieved by, for example, bilateral orchiectomy or by the administration of gonadotrophin releasing hormone (GnRH) receptor agonists.

Gonadotrophin releasing hormone (GnRH) is a natural hormone produced by the hypothalamus that interacts with a receptor in the pituitary to stimulate production of luteinising hormone (LH). To decrease LH production, agonists of the GnRH receptor (GnRH-R), such as leuprolide (Lupron) and goserelin, have been developed. Such GnRH-R agonists initially act to stimulate LH release and only after prolonged treatment act to desensitize GnRH-R such that LH is no longer produced, ultimately causing suppression of testosterone production by the testes. However, the initial stimulation of LH production by the agonist leads to an initial surge in the production of male sex hormones. This phenomenon, known as the "testosterone surge" or "flare reaction," can last for as long as two to four weeks, and may stimulate the prostate cancer; it can lead to a worsening of current symptoms or appearance of new symptoms such as spinal cord compression, bone pain and urethral obstruction. One approach that has been taken to avoid this problem has been to combine administration of a GnRH-R agonist with an antiandrogen, such as flutamide or bicalutamide, known as total androgen ablation therapy (AAT). The use of anti-androgens, however, is associated with serious hepatic and gastrointestinal side effects.

Antagonists of the gonadotrophin releasing hormone receptor (GnRH-R) have been developed to overcome the "testosterone surge" or "flare reaction" associated with GnRH agonists. GnRH antagonists competitively bind to and block the GnRH receptors and cause a rapid decrease of LH and Follicle Stimulating Hormone (FSH) excretion, thereby reducing testosterone production with no initial stimulation/surge. However, GnRH antagonist peptides are frequently associated with the occurrence of histamine-releasing activity following administration.

While the use of both GnRH agonist and antagonists in androgen deprivation therapy to treat prostate cancer has yielded promising results, there are concerns about the relative safety of the available drugs. For example, the GnRH antagonist Abarelix™ was found to carry a risk of serious allergic reactions, including anaphylaxis with hypotension and syncope, and was also found to lose efficacy over the course of treatment in some cases. Indeed, Abarelix™ (Plenaxis™ in the U.S.) was eventually approved, but only for selected patients with advanced prostate cancer, and was eventually withdrawn from the market in 2005 for commercial reasons apparently related to these problems.

The present applicants have developed a third generation GnRH antagonist, degarelix, for treatment of prostate cancer. Degarelix is a synthetic decapeptide antagonist of GnRH. A long term evaluation in a multicentre randomised study demonstrated that degarelix is effective and well-tolerated without evidence of systemic allergic reactions. An application for marketing authorisation/new drug application for a formulation for monthly administration was submitted to the FDA and EMEA on 27 Feb. 2008. Marketing Authorisation was granted by the FDA on 24 Dec. 2008, and by EMEA on 27 Feb. 2009. Currently, the one-month dosing regimen of degarelix, administered subcutaneously (s.c.) at a starting dose of 240 mg (40 mg/mL) and a maintenance dose of 80 mg (20 mg/mL), is approved in more than 50 countries including US, Canada and EU countries. The one month regimen requires monthly attendance of the patient at a hospital or clinic, where the degarelix is administered by a medical practitioner.

There is a need for a formulation which can provide sustained release of degarelix, which would therefore reduce the requirement for the patient to attend the hospital. The applicants have found that to maintain serum testosterone (in the human) below 0.5 ng/mL (i.e. to maintain the androgen deprivation therapy and prevent "testosterone breakthrough") over a longer period it is necessary to administer degarelix in such a way that the mean plasma concentration (between doses of degarelix) is maintained above 9 to 10 ng/mL. The prior (FDA, EMEA approved) formulations (e.g. the formulation for monthly administration) do not prevent testosterone breakthrough over a period of 3 months after administration. Simply increasing the amount of degarelix in the formulation, however, is not straightforward because of the risk of side effects, and also because the dose size may become unmanageable (requiring two or more injections to provide the dose). A Phase 3 one-year (active control—goserelin) trial with a 3-month degarelix dosing regimen has recently been completed. 565 patients were treated with a starting dose of 240 mg (40 mg/mL) degarelix administered subcutaneously followed by maintenance dose of 480 mg (two 240 mg injections at a concentration of 60 mg/mL) administered subcutaneously at month 1 and subsequently at 3-month intervals. No new safety issues were identified in this trial. There was a higher incidence of injection site reactions after the 480 mg maintenance doses compared to those observed after 80 mg maintenance doses associated with the one month dosing regimen.

There remains a need for a formulation which can provide sustained release of degarelix for three months or more after a single administration (e.g. a single injection). Providing such a formulation is far from straightforward, because it can be difficult to incorporate sufficient quantities of antagonist peptides (such as degarelix) into sustained release formulations [Cook and Sheridan, The Oncologist, 5:162-168 (2000)]. Further, it can be difficult to provide a formulation which provides sustained release but can also be injected through e.g. a 23 gauge needle.

According to the present invention in a first aspect there is provided a pharmaceutical formulation comprising a solid matrix of (e.g. formed from) one or more biodegradable polymers, the solid matrix including a pharmaceutically active substance or a pharmaceutically acceptable salt thereof distributed homogeneously or substantially homogeneously within the matrix; wherein the pharmaceutically active substance is gonadotropin releasing hormone (GnRH), a GnRH agonist (e.g. triptorelin) or a GnRH antagonist. The pharmaceutically active substance may be degarelix (which may be in the form of a pharmaceutically active salt of degarelix such as degarelix acetate).

The solid matrix may optionally include one or more excipients which is (are) distributed homogeneously or substantially homogeneously within the matrix. In certain embodiments, the amount of excipient(s) in the pharmaceutical formulation may be 1 to 20% by weight of the solid matrix, for example 2 to 10% (e.g. 5%) by weight of the solid matrix.

The pharmaceutically active substance or a pharmaceutically acceptable salt thereof (and excipient(s), if present) may be in the form of a solid dispersion of the pharmaceutically active substance which is distributed homogeneously or substantially homogeneously within the biodegradable polymer(s) (a solid dispersion of the pharmaceutically active substance which is distributed homogeneously or substantially homogeneously within the matrix).

Herein the term "solid", as in solid matrix, solid dispersion, or solid biodegradable polymer, refers to e.g. a polymer which is solid at ambient temperature (298K) and pressure (atmospheric pressure).

It has been proposed that degarelix is released from the known (approved) depot formulations in two phases: a fast release (also known as a burst effect or burst release) immediately after dosing, accounting for high initial plasma concentration levels; and a slow release phase which determines the plasma concentration levels in the maintenance phase. In the pharmacokinetic (PK) modelling of degarelix, these two distinct phases have been described as two first-order input phases controlling the release from the depot: a fast input to account for the initial fast release described by the fast absorption half-life and a slow input to account for the prolonged phase observed described by the slow absorption half-life. The pharmaceutical formulations of the present invention may reduce the initial burst release of degarelix from the formulation, and/or prolong the slow release phase, and thereby may provide a formulation which maintains a plasma concentration of degarelix above 9-10 ng/ml in a (e.g. human) patient for three months or more after administration. Further, the pharmaceutical formulation of the present invention may (e.g. additionally) have superior or desirable injection characteristics (e.g. be injectable through specific needles)

The (or each) biodegradable polymer may be a synthetic biodegradable polymer. The (or each) biodegradable polymer may be a biocompatible polymer. Herein the term biocompatible refers to the ability of a biomaterial to perform its desired function in a medical therapy without eliciting any undesirable local or systemic effects in the recipient or beneficiary of that therapy. The (or each) synthetic biodegradable polymer may be a polyhydroxy acid (PHA), such as poly(lactic acid) (PLA), poly(glycolic acid) (PGA), a copolymer of lactic and glycolic acid (PLGA), a copolymer of lactic and glycolic acid with poly(ethylene glycol), poly(e-caprolactone) (PCL) or poly(3-hydroxybutyrate) (PHB). The (or each) biodegradable polymer may be a natural polymer, such as a carbohydrate (such for example starch, cellulose, dextran, alginates or hyaluronates, a modified carbohydrate (such as chitin); a polypeptide; a protein, such as collagen; or a semi-synthetic polymer derived from such natural polymers, including cellulose derivatives (for example ethylcellulose, methylcellulose, ethylhydroxy-ethylcellulose and sodium carboxymethylcellulose); starch derivatives, such as hydroxyethyl starch; chitin derivatives, such as chitosan, and protein derivatives, such as gelatin.

In certain embodiments of the invention, the biodegradeable polymer (or one of the biodegradable polymers) is a copolymer of lactic and glycolic acid [(PLGA), also known as poly(lactic-co-glycolic acid)]. PLGA is biodegradable and biocompatible. PLGA is formed by copolymerisation of monomeric units of glycolic acid and lactic acid. Different forms of PLGA can be obtained by varying the ratio of lactide to glycolide used for the polymerisation, as is well known in the art, and these different forms may be identified with reference to the ratio of the monomers. Thus, "PLGA 75:25" (see Example 1a) means a copolymer having a composition which is 75% lactic acid and 25% glycolic acid. The composition of the PLGA may be denoted in terms of lactide units, referring to the percentage of lactic acid. Thus, PLGA with 50% lactide units refers to a PLGA copolymer of 50% lactic acid and 50% glycolic acid; PLGA with a composition of 75% lactide units refers to a PLGA with 75% lactic acid and 25% glycolic acid. In certain embodiments of the invention, the biodegradeable polymer is a PLGA copolymer with a molar ratio of lactic acid:glycolic acid of from 90:10 to 10:90, for example from 60:40 to 90:10, for example from 50:50 to 75:25.

In certain embodiments of the invention, the matrix is a solid matrix of a biodegradeable polymer which is a copolymer of lactic and glycolic acid (PLGA). The PLGA may have a molar ratio of lactic acid:glycolic acid of from 90:10 to 10:90, for example from 60:40 to 90:10, for example from 50:50 to 75:25.

The inherent viscosity of the biodegradeable polymer, for example the synthetic biodegradeable polymer, may be from 0.1 to 0.5 dL/g, for example from 0.1 to 0.4 dL/g, for example 0.1 to 0.2 dL/g. The applicants have found that formulations which include polymers of this viscosity may provide sustained release and may be injected through e.g. a 23 gauge needle. Surprisingly, it has been found that use of a biodegradeable polymer with low inherent viscosity will reduce the burst release from the final formulation, compared to a corresponding formulation with a polymer having higher inherent viscosity. The property of inherent viscosity of a polymer is a result of a Dilute Solution Viscosity test, which is well known and used as an indication of the molecular weight of polymers. The results of the Dilute Solution Viscosity test are expressed as Relative Viscosity, Inherent Viscosity, or Intrinsic Viscosity. The test is used for polymers that dissolve completely without chemical reaction or degradation. The polymer is first weighed and then dissolved in an appropriate solvent. The solution and a viscometer are placed in a constant temperature water bath. Thermal equilibrium is obtained within the solution. The liquid is then brought above the upper graduation mark on the viscometer. The time for the solution to flow from the upper to lower graduation marks is recorded. Viscosity may be defined as the property of resistance of flow exhibited within the body of a material. Relative Viscosity is defined as the ratio of the viscosity of the solution to the viscosity of the solvent, and Inherent Viscosity is defined as the ratio of the natural logarithm of the relative viscosity to the mass concentration of the polymer.

The pharmaceutical formulation includes a solid matrix of polymer which includes the pharmaceutically active substance (e.g. degarelix) or pharmaceutically acceptable salt homogeneously or substantially homogeneously distributed therein (that is, homogeneously distributed within the matrix)—e.g. a solid dispersion of the degarelix peptide within the matrix/polymer. Herein, the term "homogeneous" (or homogeneously) means that the distribution of the pharmaceutically active agent (e.g. degarelix or pharmaceutically acceptable salt thereof) and/or excipient(s) within the solid matrix is uniform or substantially uniform on a micrometer scale. In other words, when the formulation is studied on a micrometer scale, for example using ATR-FTIR analysis [Fourier Transform Infra Red analysis wherein Attenuated Total-internal Reflectance (ATR) of the beam within the crystal allows an IR image of the surface layer of the sample to be made, as described below], the distribution of the pharmaceutically active agent (e.g. degarelix or pharmaceutically acceptable salt thereof) and/or excipient(s) within the solid matrix appears uniform or substantially uniform (see FIG. 4, results for formulations 015A and 015E).

The applicants have found that pharmaceutical formulations of the invention may be suitable for use as sustained release formulations, for example sustained release formulations which may be administered in the form of a suspension for injection. The pharmaceutical formulations of the invention may be (e.g. in the form of a suspension) for subcutaneous (SC or s.c.) injection or, more preferably, intramuscular (IM, or i.m.) injection. The applicants have found that formulations of the invention may provide sufficient dose of degarelix in an acceptable volume (which is suitable for administration as a single injection). The formulations of the invention may provide extended release of degarelix for three months or more. Surprisingly, formulations according to the invention may maintain a plasma concentration of degarelix above 9-10 ng/ml in a patient for three months or more after administration.

In certain embodiments, the amount of degarelix in the pharmaceutical formulation may be 3 to 60% by weight of the solid matrix, for example 3 to 50% by weight of the solid matrix, for example 3 to 40% by weight of the solid matrix, for example 5 to 40% by weight of the solid matrix, for example 8 to 40% by weight of the solid matrix, for example 20 to 40% by weight of the solid matrix.

In certain embodiments, the amount of degarelix in the pharmaceutical formulation may be from 90 to 250 mg, for example from 100 to 150 mg (for a single e.g. unit dose for an adult human subject).

The pharmaceutical composition may optionally further comprise one or more excipients. The (or each) excipient may be a sugar (e.g. trehalose), a sugar alcohol (e.g. mannitol), a water soluble inorganic salt (e.g. sodium chloride), or a synthetic polymer (e.g. polyethylene oxide, PEO). It has been found that use of an excipient may improve sustained release from the final formulation.

The solid matrix may be obtained by or obtainable by a process comprising the steps of:

(a) providing in a vessel the biodegradeable polymer in solid form, the pharmaceutically active substance or salt thereof in solid form, and optionally the excipient(s);

(b) adding a solvent to the solid polymer and pharmaceutically active substance in the vessel;

(c) adding a fluid which is capable of existing in the supercritical state to the vessel;

(d) increasing the temperature and pressure in the vessel to convert the fluid to the supercritical state, optionally (e.g. actively) mixing (e.g. by agitation such as stirring) the polymer, pharmaceutically active substance and excipient(s) (if present) prior to, during, and/or after conversion of the fluid to the supercritical state;

(e) (e.g. without recovering the solid matrix,) decreasing the temperature and/or pressure in the vessel to convert the fluid to a sub-critical state; and then increasing the temperature and/or pressure in the vessel to return the fluid to the supercritical state (e.g. to remove solvent);

(f) optionally, repeating step (e) one or more (e.g. 1 to 20, e.g. 1 to 12, e.g. 10) times (e.g. to remove solvent);

(g) recovering the solid matrix;

(h) optionally, washing the solid matrix.

According to the present invention in a further aspect there is provided a pharmaceutical formulation comprising a solid matrix of (e.g. formed from) one or more biodegradable polymers, a pharmaceutically active substance or a pharmaceutically acceptable salt thereof, and optionally an excipient(s), wherein the pharmaceutically active substance is gonadotropin releasing hormone (GnRH), a GnRH agonist (e.g. triptorelin) or a GnRH antagonist (e.g. degarelix); the formulation being obtained by or obtainable by a process comprising the steps of:

(a) providing in a vessel the biodegradeable polymer in solid form, the pharmaceutically active substance or salt thereof in solid form, and optionally the excipient(s);

(b) adding a solvent to the solid polymer and pharmaceutically active substance in the vessel;

(c) adding a fluid which is capable of existing in the supercritical state to the vessel;

(d) increasing the temperature and pressure in the vessel to convert the fluid to the supercritical state, optionally (e.g. actively) mixing (e.g. by agitation such as stirring) the polymer, pharmaceutically active substance and excipient(s) (if present) prior to, during, and/or after conversion of the fluid to the supercritical state;

(e) (e.g. without recovering the solid matrix,) decreasing the temperature and/or pressure in the vessel to convert the fluid to a sub-critical state; and then increasing the temperature and/or pressure in the vessel to return the fluid to the supercritical state (e.g. to remove solvent);

(f) optionally, repeating step (e) one or more (e.g. 1 to 20, e.g. 1 to 12, e.g. 10) times (e.g. to remove solvent);

(g) recovering the solid matrix;

(h) optionally, washing the solid matrix.

The solid matrix of (e.g. formed from) one or more biodegradable polymers may include the pharmaceutically active substance or a pharmaceutically acceptable salt thereof, and/or the excipient(s) (if present), distributed homogeneously or substantially homogeneously within the matrix. The pharmaceutically active substance may be degarelix (which may be in the form of a pharmaceutically active salt of degarelix such as degarelix acetate).

The fluid may be any fluid which may be brought into the super critical state. As is known in the art, a fluid which is capable of existing in the supercritical state may be subjected to conditions of temperature and pressure up to a critical point, at which the equilibrium line between liquid and vapour regions disappears. It is well known that the fluid density and solubility properties of a supercritical fluid are liquid-like, but the viscosity, surface tension and fluid diffusion rates (in any medium) are gas-like. It is believed that the super-critical fluid penetrates the medium (the polymer) in a gas like manner, to provide the solid matrix with the pharmaceutically active substance dispersed therein.

Super critical fluids which may be used include carbon dioxide, dinitrogen oxide, water, carbon disulphide etc. In preferred examples of the invention, the fluid is carbon dioxide. The critical temperature of carbon dioxide is 304.1K and the critical pressure is 7.38 MPa. In certain embodiments, if carbon dioxide is used as the fluid, the conditions used in step (d) and (e) to convert/return carbon dioxide (the fluid) to the critical state may be a temperature within the range of from about 305 to about 333K (approximately 32 to about 60° C.) and a pressure within the range of about 7.4 to about 20.7 MPa (approximately 1073 to about 3000 psi). In certain embodiments, if carbon dioxide is used as the fluid, the conditions used in step (d) and (e) to convert/return carbon dioxide (the fluid) to the critical state may be a temperature within the range of from about 305 to about 320K (approximately 32 to about 47° C.) and a pressure within the range of about 7.4 to about 20.7 MPa (approximately 1073 to about 3000 psi).

The pharmaceutically active substance (or salt thereof) may be either soluble or insoluble in the fluid used in the process of the invention (the fluid which is capable of existing in the supercritical state). In particular examples of the invention, the pharmaceutically active substance (e.g. degarelix or salt thereof) is insoluble in the fluid used in the process of the invention (the fluid which is capable of existing in the supercritical state, e.g. carbon dioxide). In this respect, by "insoluble", it is meant that, under the supercritical conditions selected for the process, the pharmaceutically active substance (or salt thereof) has a solubility in the fluid (the fluid which is capable of existing in the supercritical state), as measured by standard techniques, such as spectroscopic measurements (e.g. utraviolet-visible or infrared spectroscopy), of less than 1 mg/mL (e.g. less than 0.1 mg/mL, such as less than 10, 8, 5, 4 or, particularly, 3, 2 or 1 µg/mL). For example, the pharmaceutically active substance (or salt thereof) may have a solubility in the fluid (the fluid which is capable of existing in the supercritical state) of less than 10 µg/mL. When the fluid selected is carbon dioxide, the solubility of the pharmaceutically active substance (or salt thereof) may, for example, be determined at a pressure of 2000 psi (13.79 MPa) and a temperature of 40° C. (313.15 K).

The supercritical conditions of step (b) may be maintained for any suitable length of time, for example for a time period of at least 1 minute (e.g. for a time period of from about 1, 2, 3, 4 or 5 to about 180 minutes, such as from about 10 or 20 to about 90 or 120 minutes or, particularly, from about 25 to 75 minutes, such as from about 30 minutes to about 60 minutes).

In step (e), the pressure may be reduced to a minimum of anywhere between ambient pressure (e.g. about 1 atmosphere) and 99% of the critical pressure for the fluid used in the process, for example a minimum within the range of from about 50 atmospheres (about 5.1 MPa) to about 95% of the critical pressure for the fluid used in the process. For example, when the fluid is carbon dioxide, the pressure in step (e) may be reduced to minimum pressure of within the range of about 6.5 to about 7.0 MPa (e.g. about 6.89 MPa (about 1000 psi)).

The variations in pressure of the fluid described in respect of step (e) may be effected either with or, particularly, without temperature control (i.e. maintaining the temperature of the mixing vessel at the same temperature as prior to step (e)). As is known to those skilled in the art, effecting pressure changes without controlling temperature will tend to lead to a drop in temperature when pressure is reduced, and an increase in temperature when pressure is increased.

Step (e), that of decreasing the temperature and/or pressure in the vessel to convert the fluid to a sub-critical state; and then increasing the temperature and/or pressure in the vessel to return the fluid to the supercritical state (e.g. without first recovering the solid matrix), may be carried out in the absence of (e.g. active) mixing (e.g. agitation such as stirring) of the polymer, pharmaceutically active substance and excipient(s) (if present) in the vessel. However, step (e) may be carried out with (e.g. active) mixing (e.g. by agitation such as stirring) of the polymer, pharmaceutically active substance and excipient(s) (if present) prior to, during, and/or after returning the fluid to the supercritical state.

Step (e), that of decreasing the temperature and/or pressure in the vessel to convert the fluid to a sub-critical state; and then increasing the temperature and/or pressure in the vessel to return the fluid to the supercritical state (e.g. without first recovering the solid matrix), may be carried out over a period of time from about 1 to about 120 minutes (e.g. from about 2 to about 60 minutes, such as from about 3 to about 30, from about 4 to about 20 or from about 5 to about 15 minutes (e.g. about 10 minutes)).

Optional step (f) of the process of the invention repeats the cycle of step (c). For the avoidance of doubt, each repetition may be the same or different.

The applicants have found that there is little, if any, degradation of degarelix (for example, 0 to 1.5% degradation of degarelix) following exposure to supercritical carbon dioxide.

The solvent added in step (b) is used as a processing aid. In certain embodiments, the solvent is a solvent which is miscible in the fluid (which is capable of existing in the supercritical state, e.g. carbon dioxide). In certain embodiments, the solvent is a solvent in which the pharmaceutically active substance (or salt thereof) is soluble. Conventional solvents that may be used include aprotic organic solvents such as dimetholsufoxide (DMSO), acetone or alcohols such as ethanol, organic acids such as acetic acid. The applicants have found that adding the solvent to the biodegradable polymer and the pharmaceutically active substance in solid form, and subsequently adding the fluid and converting the fluid to the super critical state, may aid in the homogeneous or substantially homogeneous distribution (e.g. solid dispersion) of the pharmaceutically active substance (and excipient(s) if present) within the matrix. Without being bound by theory, it is believed that the supercritical carbon dioxide/solvent (DMSO) mixture may dissolve, or liquify, the pharmaceutically active substance (e.g. peptide, e.g. degarelix) and allow formation of a solid dispersion of the peptide within the polymer (matrix). The applicants have found that in certain examples DMSO is particularly effective because DMSO is miscible in the fluid which is capable of existing in the supercritical state (carbon dioxide), and the pharmaceutically active substance (degarelix, e.g. degarelix acetate) is soluble in DMSO. The pharmaceutically active substance (degarelix, e.g. degarelix acetate) may be insoluble in the fluid which is capable of existing in the supercritical state (carbon dioxide). Degarelix, e.g. degarelix acetate, is insoluble in the fluid which is capable of existing in the supercritical state (carbon dioxide).

It will be appreciated that step (e) (decreasing the temperature and/or pressure in the vessel to convert the fluid to a sub critical state; and then increasing the temperature and/or pressure in the vessel to return the fluid to a super critical state) is done without recovering the polymer matrix after step (d). The term "without recovering" means that the polymer matrix is not removed from the vessel before this step. Thus, the solid matrix is not recovered between the step where it is converted to a super critical state (step (d)) and step (e) where it is converted to a sub critical state and subsequently returned to the super critical state. The conditions used in step (g) to recover the solid matrix, for example by releasing the pressure in the vessel (e.g. to spray the matrix from the vessel), may be manipulated to control the size of the solid matrix, as is well known in the art. The solid matrix may be recovered in the form of microparticles, may be recovered in a larger form (e.g as a pellet) which may be ground down (or subject to other size reduction process) to form microparticles, etc.

The solid matrix may be in the form of microparticles. The microparticles may have mean particle size of from about 2 to about 300 µm, such as from about 10 to about 150 µm, or from about 25 to about 100 µm, or from about 25 to about 65 µm, or from about 30 to about 60 µm [expressed as the volume mean diameter (VMD)]. The volume mean diameter of the microparticles is well known and is readily measured by techniques known in the art such as laser diffraction, see for example Example 1a below and table therein.

The microparticles may have a mean particle size expressed as the volume mean diameter (VMD) of from about 2, 3, 4, 5, 8 or 10 to about 500 µm, such as from about 20 to about 200 or 250 µm, from about 25 to about 150 µm, from about 30 to 100 µm, or, particularly, from about 35 to about 80 µm. In more particular examples of the invention, no more than 10% of the microparticles have a diameter ($D_{10\%}$) less than the lower limit of each of the size ranges quoted above respectively and at least 90% of the particles have a diameter ($D_{90\%}$) that does not exceed the upper limit of each of the size ranges quoted above respectively.

In certain embodiments of the invention, the solid matrix (e.g. microparticles) is washed. The solid matrix (microparticles) may be washed in water, a $C_1$ to $C_8$ alcohol (e.g. ethanol, methanol) or a solution of a $C_1$ to $C_8$ alcohol (e.g. ethanol, methanol) in water. Applicants have found that washing the formulation may increase sustained release (reduce the burst release) from the formulation.

According to the present invention in a further aspect there is provided a pharmaceutical formulation comprising a solid matrix of (e.g. formed from) one or more biodegradable polymers (e.g. synthetic biodegradeable polymers) having inherent viscosity from 0.1 to 0.5 dL/g; the solid matrix including a pharmaceutically active substance or a pharmaceutically acceptable salt thereof and optionally an excipient(s), wherein the pharmaceutically active substance is gonadotropin releasing hormone (GnRH), a GnRH agonist (e.g. triptorelin) or a GnRH antagonist. The inherent viscosity of the biodegradeable polymer(s) may be from 0.1 to 0.5 dL/g, for example from 0.1 to 0.4 dL/g, for example 0.1 to 0.2 dL/g. The pharmaceutically active substance may be degarelix (which may be in the form of a pharmaceutically active salt of degarelix such as degarelix acetate). The biodegradeable polymer(s) may be as described above for other aspects of the invention. The formulation may be made by the method(s) according to the invention. The solid matrix of (e.g. formed from) one or more biodegradable polymers may include the pharmaceutically active substance or a pharmaceutically acceptable salt thereof, and/or an excipient(s) (if present), distributed homogeneously or substantially homogeneously within the matrix. Inherent viscosity is discussed above. The pharmaceutical formulation may be (e.g. in the form of a suspension) for subcutaneous (SC or s.c.) injection or, more preferably, intramuscular (IM, or i.m.) injection.

According to the present invention in a further aspect there is provided a pharmaceutical formulation comprising a solid matrix of (e.g. formed from) one or more biodegradable polymers, the solid matrix including a pharmaceutically active substance or a pharmaceutically acceptable salt thereof distributed homogeneously or substantially homogeneously within the matrix; wherein the pharmaceutically active substance is gonadotropin releasing hormone (GnRH), a GnRH agonist (e.g. triptorelin), a GnRH antagonist (e.g. degarelix, e.g. degarelix acetate), a growth hormone (such as bovine growth hormone, human growth hormone, hGH, recombinant hGH), growth hormone releasing factor, somatostatin, vasopressin, a vasopressin analog (e.g. desmopressin, desmopressin acetate), glucagon-like peptide-1 (GLP-1), glucagon-like peptide-2 (GLP-2), prolactin, octreotide (e.g. octreotide acetate), oxytocin or analog thereof (e.g. carbetocin), human menopausal gonadotropin (HMG), luteinizing hormone (LH), follicle-stimulating hormone (FSH), human chorionic gonadotropin (hCG), or anti-IL-6 agent (IL-6 inhibitor). The pharmaceutically active substance may be degarelix (which may be in the form of a pharmaceutically active salt of degarelix such as degarelix acetate). The biodegradeable polymer(s) may be as described above for other aspects of the invention. The biodegradeable polymer(s) may have inherent viscosity from 0.1 to 0.5 dL/g, for example from 0.1 to 0.4 dL/g, for example 0.1 to 0.2 dL/g. Inherent viscosity is discussed above. The formulation may be made by the method(s) according to the invention (e.g. as described above). The solid matrix may optionally include one or more excipients which is (are) distributed homogeneously or substantially homogeneously within the matrix. In certain embodiments, the amount of excipient in the pharmaceutical formulation may be 1 to 20% by weight of the solid matrix, for example 2 to 10% (e.g. 5%) by weight of the solid matrix. The pharmaceutical formulation may be (e.g. in the form of a suspension) for subcutaneous (SC or s.c.) injection or, more preferably, intramuscular (IM, or i.m.) injection.

According to the present invention in a further aspect there is provided a pharmaceutical formulation comprising a solid matrix of (e.g. formed from) one or more biodegradable polymers, the solid matrix including a pharmaceutically active substance or a pharmaceutically acceptable salt thereof distributed homogeneously or substantially homogeneously within the matrix; wherein the pharmaceutically active substance is a peptide or other molecule which is prone to aggregation. Herein, the terminology "prone to aggregation" means the peptide/molecule is prone to forming a layer of peptide (molecule) at the surface of the mixture, if it is mixed with a biodegradable polymer. The pharmaceutically active substance may be degarelix (which may be in the form of a pharmaceutically active salt of degarelix such as degarelix acetate). The applicants have found that it is possible to formulate such peptides (e.g. degarelix) without (or with reduced) aggregation (i.e. without, or with reduced, formation of a layer of peptide (e.g. degarelix) at the surface of the mixture, when it is mixed with the biodegradable polymer). The biodegradeable polymer(s) may be as described above for other aspects of the invention. The biodegradeable polymer(s) may have inherent viscosity from 0.1 to 0.5 dL/g, for example from 0.1 to 0.4 dL/g, for example 0.1 to 0.2 dL/g. Inherent viscosity is discussed above. The formulation may be made by the method(s) according to the invention (e.g. as described above). The solid matrix may optionally include one or more excipients which is (are) distributed homogeneously or substantially homogeneously within the matrix. In certain embodiments, the amount of excipient in the pharmaceutical formulation may be 1 to 20% by weight of the solid matrix, for example 2 to 10% (e.g. 5%) by weight of the solid matrix. The pharmaceutical formulation may be (e.g. in the form of a suspension) for subcutaneous (SC or s.c.) injection or, more preferably, intramuscular (IM, or i.m.) injection.

The formulations/solid matrices of the invention may be "true blends" as opposed to phase-separated blends. Differential scanning calorimetry (DSC) can be used to determine whether a true blend or a phase separated blend is obtained, as is well known in the art. The or each solid polymer present in the formulations/solid matrices of the invention will have a glass transition temperature ($T_g$), a melting temperature ($T_m$) or both a $T_g$ and $T_m$. A true-blended composition displays a single $T_g$ (as measured by DSC) for the blend of solid polymers. In contrast, in a phase-separated blend, the $T_g$ of the or each solid polymer component will tend to remain distinct from the or each $T_g$ of the other solid polymer components.

The applicants have found that formulations/solid matrices of the invention may typically have $T_g$ in the range 40 to 55, for example $T_g$ 45 to 50, for example a $T_g$ of 47° C. as measured by DSC when heated from −20-100° C. at 10° C/min. For example, a formulation/matrix of the invention including 55% polymer PLGA 75:25, 40% degarelix loading, and 5% trehalose typically has a $T_g$ of 47° C. as measured by DSC when heated from −20-100° C. at 10° C./min.

The pharmaceutical formulation may be for, or for use in, the treatment of prostate cancer or benign prostate hyperplasia. The present invention also provides the use of a pharmaceutical formulation described herein (according to aspects of the invention) for, or in the manufacture of a medicament for, the treatment of prostate cancer or benign prostate hyperplasia (BPH).

According to the present invention in a further aspect there is provided a method of treatment of prostate cancer or BPH comprising a step of administering to a patient in need thereof a pharmaceutical preparation according to the invention.

The pharmaceutical formulation of the present invention may be for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical pharmaceutical formulation comprises a pharmaceutically acceptable carrier, such as a solution or liquid [e.g. aqueous solution, water such as water for injection (WFI), or e.g. an oily vehicle such as sesame oil), non toxic ingredient(s), including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

The pharmaceutical formulation(s) of the invention may further comprise a pharmaceutically acceptable carrier, for example an aqueous carrier or an oily vehicle.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), injectible organic esters such as ethyl oleate, pharmaceutically acceptable surfactants etc.

The formulations of the present invention may also contain additives such as but not limited to preservatives, wetting agents, emulsifying agents, and dispersing agents. Antibacterial and antifungal agents can be included to prevent growth of microbes and includes, for example, m-cresol, benzyl alcohol, paraben, chlorobutanol, phenol, sorbic acid, and the like. Furthermore, it may be desirable to include isotonic agents such as sugars, sodium chloride, and the like.

In certain embodiments, the pharmaceutical formulation may be a suspension (in a liquid such as water) for injection, e.g. SC or IM injection. Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

The pharmaceutical formulation (e.g. injectable formulation) of the invention may be supplied as a product which includes one or more doses of the pharmaceutical formulation. The product can be supplied in any appropriate package. For example, a product can contain a number of pre-filled syringes or vials containing the pharmaceutical formulation of the invention. The syringes or vials may be packaged in a blister package or other means to maintain sterility. A product can optionally contain instructions for using the formulation. The pH and exact concentration of the various components of the pharmaceutical composition may be adjusted in accordance with routine practice in this field. See GOODMAN and GILMAN's THE PHARMACOLOGICAL BASIS FOR THERAPEUTICES, $7^{th}$ ed.

DETAILED DESCRIPTION OF THE INVENTION

The present invention will now be described in detail with reference to the attached drawings in which.

Figure 4:
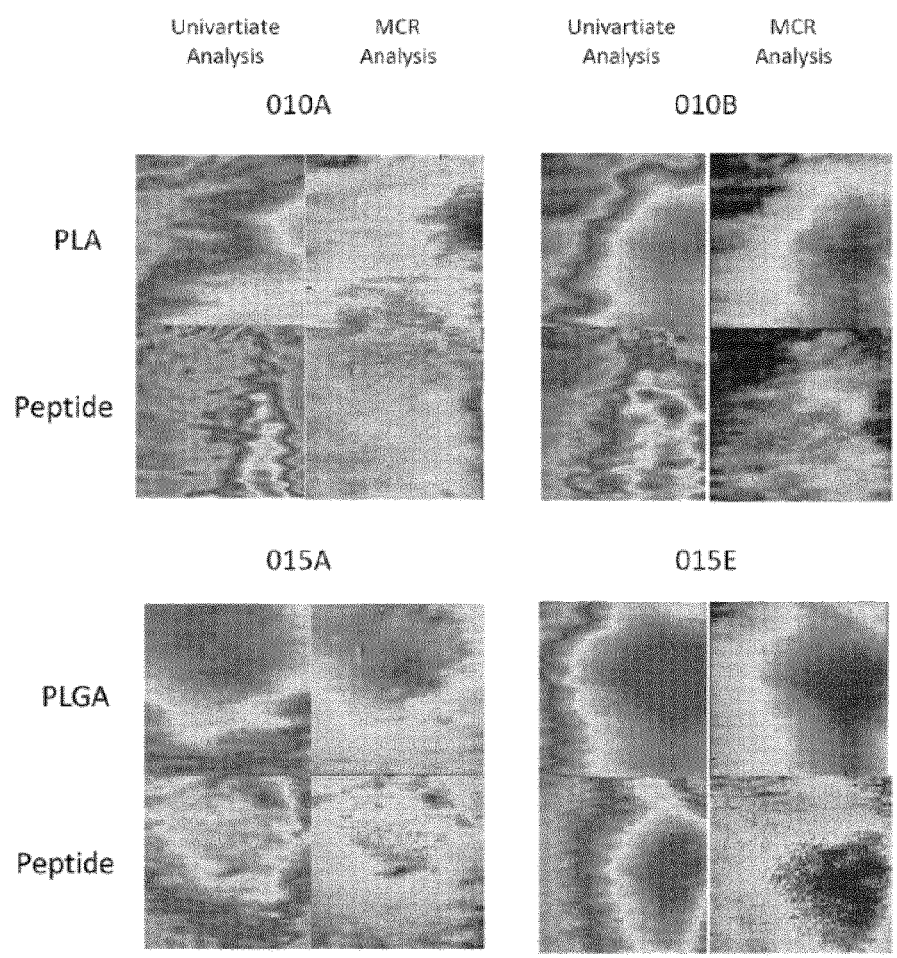
Figure 5:
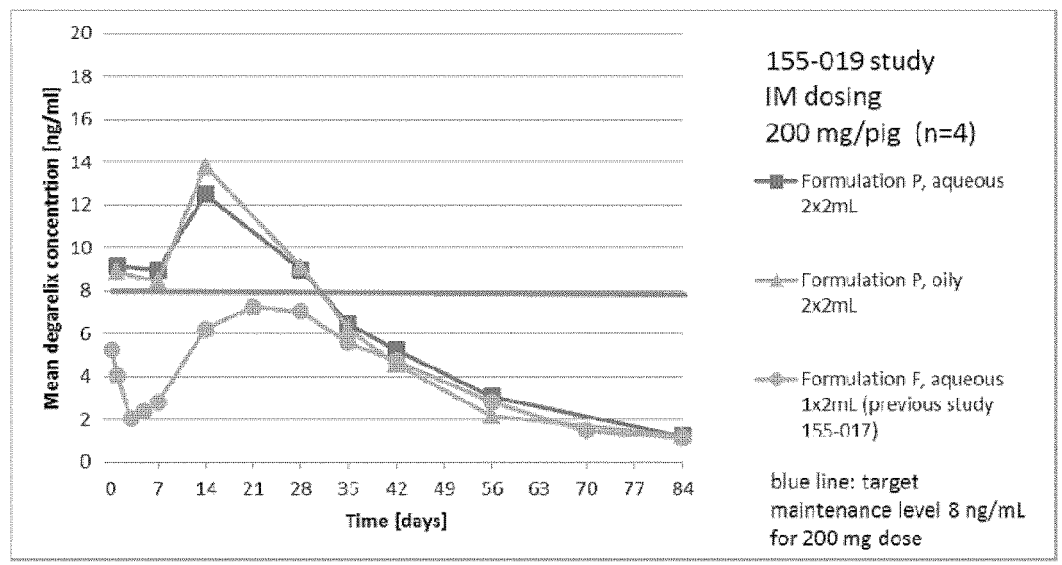

FIG. 4 shows ATR-IR images of microparticles of formulations of certain aspects of the invention [formulations 015A and 015E] compared to other formulations, in the dry state, looking at peptide (i.e. degarelix) distribution; and FIG. 5 shows the mean degarelix plasma concentration (ng/L) vs time for formulations P of the invention in aqueous vehicle (squares) and oily vehicle (triangles) versus a reference F (circles) following intramuscular injection in an in vivo study in a pig model.

DEFINITIONS

The term "prostate cancer" refers to any cancer of the prostate gland in which cells of the prostate mutate and begin to multiply out of control. The term "prostate cancer" includes early stage, localized, cancer of the prostate gland; later stage, locally advanced cancer of the prostate gland; and metastatic stage cancer of the prostate gland (in which the cancer cells spread (metastasize) from the prostate to other parts of the body, especially the bones and lymph nodes).

Degarelix and Related Pharmaceutical Formulations

Degarelix is a potent GnRH antagonist that is an analog of the GnRH decapeptide (pGlu-His-Trp-Ser-Tyr-Gly-Leu-Arg-Pro-Gly-NH$_2$) incorporating p-ureido-phenylalanines at positions 5 and 6 (Jiang et al. (2001) *J. Med. Chem.* 44:453-67). It is indicated for treatment of patients with prostate cancer in whom androgen deprivation is warranted (including patients with rising PSA levels after having already undergone prostatectomy or radiotherapy).

Degarelix is a selective GnRH receptor antagonist (blocker) that competitively and reversibly binds to the pituitary GnRH receptors, thereby rapidly reducing the release of gonadotrophins and consequently testosterone (T). Prostate cancer is sensitive to testosterone deprivation, a mainstay principle in the treatment of hormone-sensitive prostate cancer. Unlike GnRH agonists, GnRH receptor blockers do not induce a luteinizing hormone (LH) surge with subsequent testosterone surge/tumor stimulation and potential symptomatic flare after the initiation of treatment.

The active ingredient degarelix is a synthetic linear decapeptide amide containing seven unnatural amino acids, five of which are D-amino acids. The drug substance is an acetate salt, but the active moiety of the substance is degarelix as the free base. The acetate salt of degarelix is a white to off-white amorphous powder (of low density as obtained after lyophilisation). The chemical name is D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4-pyrimidinyl]carbonyl]amino]-L-phenylalanyl-4-[(aminocarbonyl)amino]-D-phenylalanyl-L leucyl-N6-(1-methylethyl)-L-lysyl-L-prolyl. It has an empirical formula of $C_{82}H_{103}N_{18}O_{16}Cl$ and a molecular weight of 1,632.3 Da. The chemical structure of degarelix has been previously shown (EP 1003774, U.S. Pat. No. 5,925,730, U.S. Pat. No. 6,214,798) and may be represented by the formula:

Ac-D-2Nal-D-4Cpa-D-3Pal-Ser-4Aph(Hor)-D-4Aph(Cbm)-Leu-Lys(iPr)-Pro-D-Ala-N H$_2$.

The present invention provides novel formulations which provide more sustained release.

WORKED EXAMPLES

Degarelix was supplied by Ferring Pharmaceuticals, Denmark. PLGA and PLA were supplied by Evonic, Germany & USA. All other reagents were analytical grade and obtained from Fisher Scientific, UK. All materials were used as received. Chromatography was performed using a YMC Basic column (S-5 µm, 250×3.0 mm) purchased from Hichrom Ltd, UK.

Example 1a

Degarelix Processed with DMSO and Pressure Cycling
Method

PLGA 75:25 ($M_w$ 8 kDa, measured in THF relative to PS standards, 1.89 g) was mixed with Degarelix (0.21 g, 10 wt. %) by shaking/inverting the weighting vial containing both components. This mixture was loaded in to a vessel in the form of a supercritical fluid PGSS processing apparatus (see, for example, *J. Pharm. Sci.,* 93(4), 1083-1090 (2004)). DMSO (350 µL) solvent was added to the system as an aid to processing. The rig was sealed and pressurised with $CO_2$. The temperature and pressure were raised to approximately 40° C. and 2000 psi rendering the $CO_2$ a supercritical fluid. Whilst maintaining these conditions the PLGA and Degarelix were mixed for 30 min with a mechanical stirrer that formed part of the PGSS processing apparatus. Mixing was then ceased and the contents of the rig were subjected to 10 pressure cycles. Each pressure cycle lasted a total of 20 minutes and consisted of the pressure being decreased gradually to approximately 1000 psi and then immediately increased abruptly to re-achieve the desired system pressure. After completion of the 10 pressure cycles, the system was depressurised and the product was collected and ground to obtain a free flowing powder.

Particle Size Measurements

Measurements relating to particle size (e.g. VMD, d90, d50 and d10) were obtained by laser diffraction using a Sympatec Helos particle sizing apparatus with an R5 (1-1000 µm) lens. All particle sizes were measured in DI water with 10 drops of a 1% v/v Tween®20.

| Polymer | API | Processing Aid/solvent | VMD (microns) | d90 (microns) | d50 (microns) | d10 (microns) |
|---|---|---|---|---|---|---|
| PLGA 8 kDa | Degarelix 10 wt % | DMSO | 68.67 | 125.05 | 58.67 | 22.58 |

In Vitro Release Testing

In-vitro release of microparticles is conducted with a manitol/acetate buffer solution at pH 4. 1 mL of this buffer is added to 10 mg of microparticles in a 1.5 mL Eppendorf tube and rotated at 10 rpm in an incubator at 37° C. Each sample is analysed in triplicate. At a time point a sample is removed and centrifuged at 8000 rpm for 3 min. 800 µL of supernatant is removed which is further centrifuged at 13000 rpm for 3 min to acquire a 200 µL sample for HPLC analysis. The supernatant is replaced with fresh buffer and the sample placed back in the incubator.

Loading is calculated separately from the release samples using an anti-solvent precipitation method. A 25 mg sample is weighed out into a 25 mL volumetric flask. 1 mL of acetone is added to the volumetric flask to dissolve the microparticles. Once dissolved, the volumetric flask is topped up with water (approximately 24 mL), precipitating the polymer. A 1 mL sample of the supernatant is taken and centrifuged at 13000 rpm for 3 min. From this, a 200 µL sample is taken and analysed by HPLC. The loading determination method is carried out in triplicate and an average is taken.

Example 1b

Degarelix Processed with DMSO but Without Pressure Cycling
Method

The method used in this reference example was identical to that described in respect of Reference Example 1a above, except that:
(i) only 20 µL of DMSO (instead of 350 µL of DMSO) was added as a processing aid at the beginning of the process; and
(ii) the 10 pressure cycles were omitted.

Results

Figure 1:
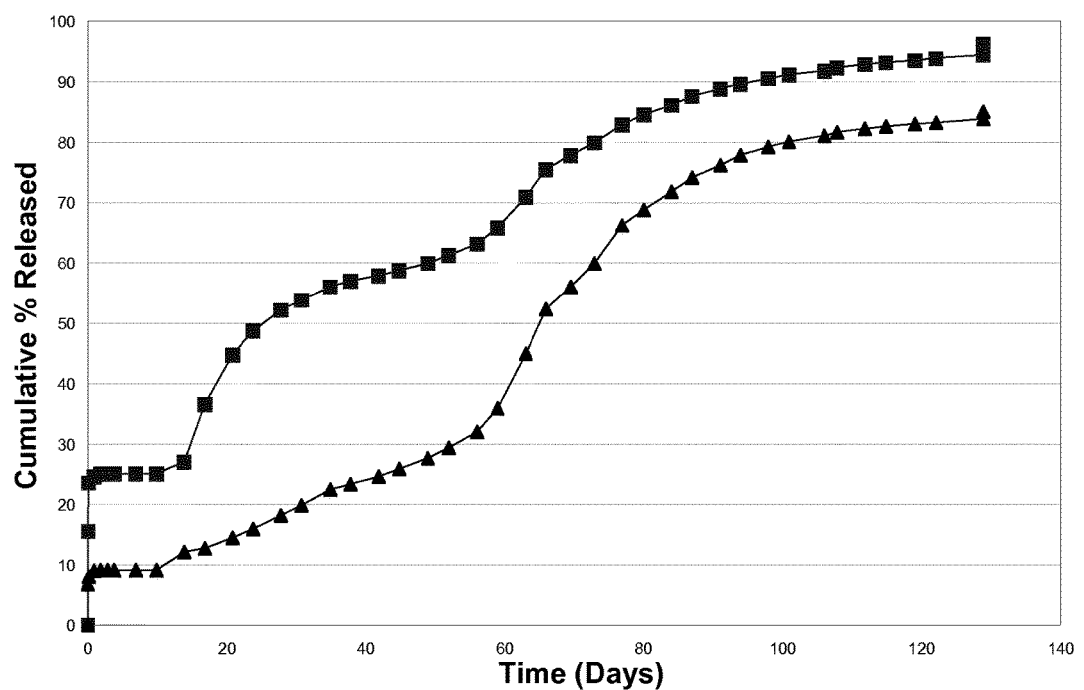
FIG. 1 shows the cumulative release of degarelix in vitro from a polymer formulation prepared with a processing aid (DMSO) and either with (lower line) or without (upper line) the use of pressure cycling. As can be seen from the graph of FIG. 1, the effect of 10 pressure cycles (lower line) was a decrease of approximately 15% in the initial burst release of degarelix from the formulation.

Release of degarelix from the formulations of Examples 1a and 1b was measured according to the method described above. The release profile observed is illustrated in FIG. 1. As can be seen from the graph of FIG. 1, the effect of 10 pressure cycles (Example 1a, lower line) was a decrease of approximately 15% in the initial burst release of degarelix from the formulation.

Example 2

Batch Manufacture

A typical batch was prepared by adding 2.1 g of pre-weighed polymer and Degarelix into the supercritical processing apparatus (vessel—see Example 1a). Peptide nominal loading was from 10 to 40% w/w of the formulation. 350 µL of DMSO solvent was then added on top of this mixture in the mixing chamber. The vessel was sealed, CO2 added to ~50 bar (5 MPa) and the system heated to 40° C. Once at the desired temperature the pressure was increased to 140 bar (14 MPa) with additional CO2. Under the processing conditions, the polymer component of the formulation liquefied due to depression of the glass by the addition of CO2. The liquefied polymer/degarelix mixture was then stirred at 150 rpm for 30 minutes, after which time stirring was stopped and pressure cycling, using depressurisation followed by re-pressurisation with fresh CO2, was used to remove the DMSO. The pressure of the system was decreased to ~70 bar (7 MPa) then increased to 140 bar (14 MPa). This cycle was repeated 10 times. The mixture was stirred briefly after each cycle. CO2 was vented through water to trap any removed DMSO. The system was then depressurised and the mixed formulation was recovered from the mixing chamber.

The formulation was then ground into microparticles using a pestle and mortar. After manufacturing, the particles were sieved to remove any particles larger than 100 µm. Batches were sieved through a 100 µm sieve using a Retsch sieve shaker at an amplitude of 1.5 mm for 30 min.

The microparticles are suitable for suspension in e.g. water or oil such as sesame oil, and subsequent subcutaneous or intramuscular injection. The microparticles may also be washed, as follows.

Washing

Degarelix loaded microparticles were washed in an ethanol solution containing 10% v/v water for 1 to 15 min depending on the encapsulating polymer. 200 mg of microparticles were washed in 100 mL of this solution. The microparticles were subsequently filtered and then dried under vacuum for at least 2 hours. The resultant cake was re-ground into microparticles using a pestle and mortar, and the particles were sieved to remove any particles larger than 100 µm. Batches were sieved through a 100 µm sieve using a Retsch sieve shaker at an amplitude of 1.5 mm for 30 min.

The washed microparticles are suitable for suspension in e.g. water or oil such as sesame oil, and subsequent subcutaneous or intramuscular injection.

ATR-IR images obtained (see FIG. 4 and associated text) reveal that the formulations made using the method of Example 2 have a substantially homogeneous distribution of Degarelix. It is believed that loading solvent to the dry degarelix and dry polymer (and excipient if present) may improve the homogeneity of the distribution.

Further Examples and In Vivo Testing in Rat Model

Examples for testing were made according to the method of Example 2. Table 1 shows the compositions of five further examples of formulations of the invention. Example D40W was made by the method of Example 2 using a PLGA 50:50, and including the step of washing in ethanol solution.

Examples 21F, 21G, 21N and 21P were also made by the method of Example 2 using a PLGA 75:25 or PLGA 50:50, but with addition of either trehalose excipient for Examples 21G, 21N and 21P, or mannitol excipient for Example 21F. The excipient was added in an amount of approximately 5% by weight of the solid matrix. Examples 21P and 21N were washed in ethanol solution, as described in Example 2.

TABLE 1

Figure 2:
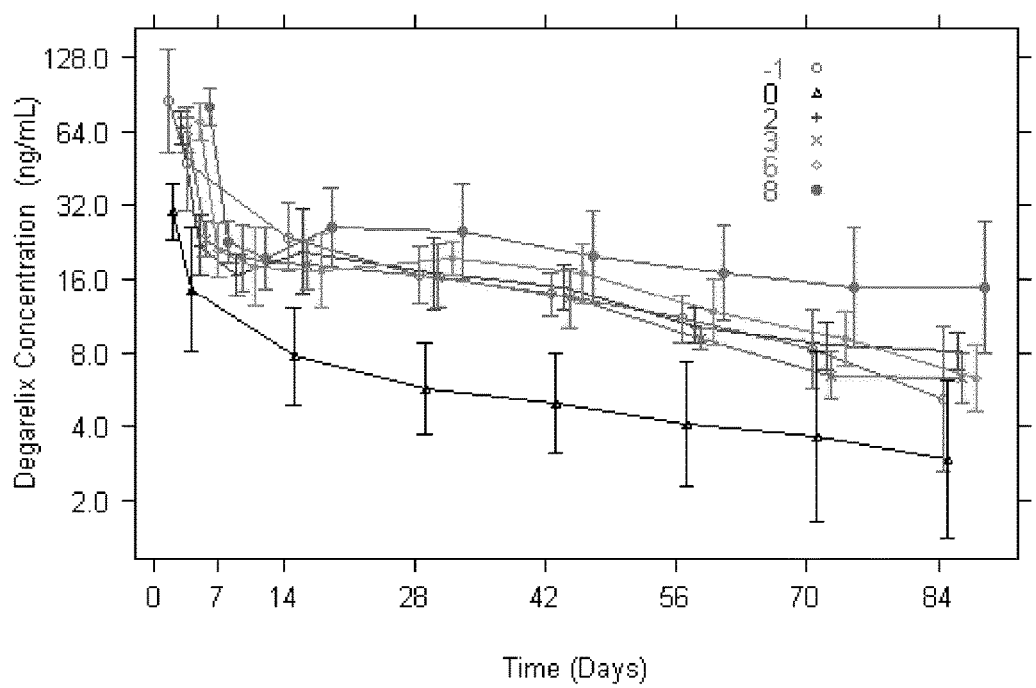
FIG. 2 shows the mean degarelix plasma concentration (ng/L) vs time for formulations of the invention 21F (+), 21G (X), 21P (solid circle), 21N (diamond), versus the subcutaneous reference (open triangle) and intramuscular reference (open circle) in an in vivo study in the rat.
Figure 3:
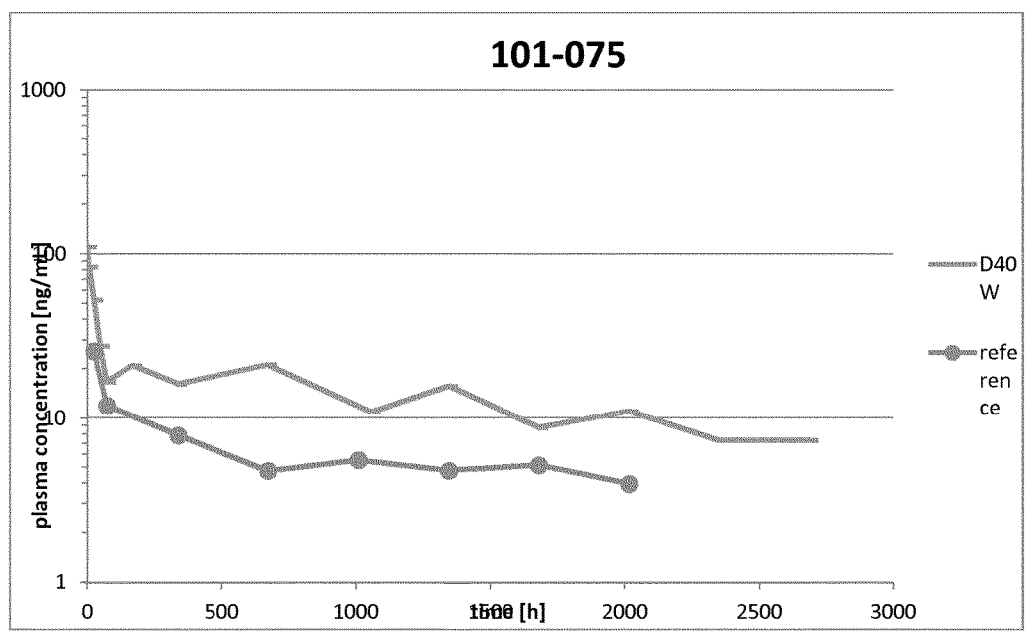
FIG. 3 shows the mean degarelix plasma concentration (ng/L) vs time for formulation of the invention D40W, versus the subcutaneous reference (circle) in an in vivo study in the rat.

| Example | PLGA lactate units % | Inherent viscosity (dL/g) | Other variants (excipient included, washing) | Degarelix load in particles | Notation in FIG. 2 |
|---------|----------------------|---------------------------|----------------------------------------------|----------------------------|---------------------|
| D40W | 50 | 0.1 | Washed | 15* | Not shown in FIG. 2; see FIG. 3 |
| 21F | 75 | 0.1 | Mannitol excipient | 36 | + |
| 21G | 75 | 0.1 | Trehalose excipient | 38 | X |
| 21P | 75 | 0.1 | Trehalose excipient/ washed | 8* | Solid circle |
| 21N | 50 | 0.2 | Trehalose excipient/ washed | 10* | diamond |

*See note "Improved Analytics" below

Degarelix may be provided as a powder for reconstitution (with a solvent) as solution for subcutaneous injection. The powder may be provided as a lyophilisate containing degarelix (e.g. as acetate) and mannitol. A suitable solvent is water (e.g., water for injection, or WFI). The solvent may be provided in vessels (e.g. vials), e.g. containing 6 mL solvent. For example, degarelix may be provided in a vial containing 120 mg degarelix (acetate) for reconstitution with 3 mL WFI such that each mL of solution contains about 40 mg degarelix; reconstituting gives a 3 mL solution for injection containing about 120 mg degarelix. Injection of two such solutions provides a starting dose of about 240 mg degarelix of concentration 40 mg/mL. The reconstituted solution ready for injection should be perceived as a visually clear liquid. The reference for the study was made by this method.

The in vivo pharmacokinetic study was performed in the Ferring NOD-lab (Arhus, DK). A fixed dose of one of the formulations (D40W, 21F, 21G, 21P, 21N) was administered to a rat at a dose of about 5 mg degarelix per rat, by subcutaneous injection using a 21G needle. The D40W formulation was administered to four rats, and data gathered to four months post administration. The other formulations were administered to six rats (each), and data gathered to three months post administration. Bioanalysis was carried out at the Ferring International Pharmascience Centre (Copenhagen, DK). A control subcutaneous formulation (reference) and control intramuscular formulation were also administered to rats in the control group.

The applicants have found that to maintain serum testosterone (in the human) below 0.5 ng/mL (i.e. to maintain the androgen deprivation therapy and prevent "testosterone breakthrough") it is necessary to administer degarelix in such a way that the mean plasma concentration (between doses of degarelix) is maintained above 9 to 10 ng/mL. In the rat, the mean plasma concentration level of degarelix which is necessary to ensure there is no testosterone breakthrough between doses is 6 ng/mL, and this value was therefore selected as the target level for the present work. In other words, if the mean plasma concentration of degarelix is 6 ng/mL or greater after administration of a given formula, this is a good indicator that the formulation would be effective (for the duration of the study).

FIG. 2 shows the mean plasma degarelix concentration (ng/L) vs time for formulations of the invention 21F (+), 21G (X), 21P (solid circle), 21N (diamond), versus the subcutaneous reference (open triangle) and intramuscular reference (open circle). All formulations of the invention had mean degarelix concentration well above the 6 ng/L target level at (or after) 84 days; the reference formulations did not.

The best formulation included low inherent viscosity polymer and trehalose excipient, and had been washed (formulation 21P).

It is believed that aggregation of degarelix around the outside of the matrix/microparticle may provide a protective shell that can restrict degarelix release and/or prevent polymer degradation, which may result in an unsatisfactory formulation and degarelix release profile (results not shown). The applicants have found that inclusion of an excipient within the matrix (e.g. trehalose, mannitol) reduces the aggregation of degarelix, and provides a formulation which maintains mean degarelix concentration well above the 6 ng/L target level until (or after) 84 days after administration (formulation 21F, 21G). The applicants have found that the process of washing in ethanol also provides a formulation which maintains mean degarelix concentration well above the 6 ng/L target level until over 84 days after administration (see D40W, FIG. 3). The results for Formulation 21P indicate that the effect may be cumulative.

Formulation 21N (higher inherent viscosity polymer, lower lactide content) was not quite as good as formulation 21P. Other experiments (results not shown) have indicated that inclusion of a lower inherent viscosity polymer correlates well with reduced burst release, while there is no correlation between burst release and lactide/glycolide content. As shown in FIG. 3 (see below) lower inherent viscosity (IV) polymers are now displaying good performance in vivo with elevated serum levels of Degarelix over time periods up to 4 months. This is a somewhat surprising observation that lower IV polymers should be used to achieve extended elevated serum levels (by reducing the burst release). However, it is believed that degarelix peptide aggregating around the microparticle may provide a protective shell that may restrict degarelix release and/or prevent polymer degradation (results not shown). If this is the case, it follows that a more rapidly degrading polymer (i.e. a low IV polymer) may be beneficial.

FIG. 3 shows a plot (dose corrected) of the mean degarelix plasma concentration (ng/L) vs time (hours) for formulation of the invention D40W and the subcutaneous reference (circle). Referring to the timepoints, 2000 hours is approximately 83 days (2.7 months); 2700 hours is approximately 113 days, or 3.7 months. The D40W formulation, which includes a lower IV polymer, performed extremely well, and it meets the target for serum levels even out to 4 months after administration.

Improved Analytics

The "Degarelix load" in the particles described in Table 1 above was determined following a classical polymer precipitation method and removal of the supernatant for peptide assay. As the variability of the method was quite high and the efficiency lower than 100%, an improved method was developed using a biphasic loading method. Briefly, the microparticles are first dissolved in acetonitrile and chloroform and topped with 0.1% phosphoric acid. After stirring, a sample is taken from the aqueous layer, centrifuged and diluted for assay determination. This new method affected greatly the outcome of peptide load data of the washed formulations, as shown in Table 2 below:

TABLE 2

| Sample | | New method | | | Old Method |
| --- | --- | --- | --- | --- | --- |
| | | Load | SD | RSD | Load |
| 21F | | 39% | 0.02 | 4.26% | 32% |
| 21G | | 40% | 0.03 | 7.18% | 36% |
| 21P | Washed | 35% | 0.01 | 2.74% | 8% |
| D40W | Washed | 37% | 0.01 | 2.93% | 15% |

It can be seen that the calculated load (that is, the degarelix load) for samples 21F and 21G was consistent when calculated by both the new and old methods, but the load (degarelix load) calculated by the new method for samples 21P and D40W was markedly increased compared to the old method. As a result, the applicants found that samples D40W, 21P (and 21N) were administered in the rat study above at 2 to 4 times the nominal dose (although F and G were correctly dosed). As a result, care should be exercised in interpreting the results above and set out in FIGS. 2 and 3.

Appendix-ATR-FTIR Spatial Distribution Determination

Attenuated total reflectance (ATR) is a well known sampling technique used in conjunction with infrared spectroscopy which enables samples to be examined directly in the solid (or liquid) state without further preparation.

ATR uses a property of total internal reflection resulting in an evanescent wave. A beam of infrared light is passed through an ATR crystal (e.g. germainum, zinc selenide) in such a way that it reflects at least once off the internal surface which in contact with the sample. This reflection forms the evanescent wave which extends into the sample. The penetration depth into the sample is typically between 0.5 and 2 micrometres, with the exact value being determined by the wavelength of light, the angle of incidence and the indices of refraction for the ATR crystal and the medium being probed. The beam is then collected by a detector as it exits the crystal.

In the case of a solid sample, as here, the sample is pressed into direct contact with the crystal. This is because the evanescent wave into the solid sample is improved with a more intimate contact, and also to ensure that trapped air is not the medium through which the evanescent wave travels (which would distort the results).

The distribution of Degarelix throughout two microparticle formulations was analysed using IR imaging. This technique compresses the sample against a crystal surface and the IR beam is passed through the crystal. Attenuated Total-internal Reflectance (ATR) of the beam within the crystal allows an IR image of the surface layer of the sample (up to a few microns thick) pressed against the crystal to be obtained. Each pixel of the image consists of an IR spectrum. Data was processed using two methods, Univariate and Multivariate Curve Resolution (MCR) analysis. Univariate analysis picks a signature peak for each substance of interest and then displays the relative intensity of this peak for each pixel of the image. MCR analysis averages the spectra over the whole image, and then deconvolutes this average spectrum into factors. Using knowledge of the formulation composition, these factors can then be assigned to formulation components and images produced of these components at each pixel.

Comparison of the images obtained (FIG. 4) revealed that the formulations according to an aspect of the invention [formulations 015A and 015E] had a homogeneous distribution of degarelix peptide (shown by ATR-FTIR on a micrometer scale); this was in contrast to the 010A and 010B formulations which were less homogeneous. It was not possible to distinguish between formulations 015A and 015E in terms of homogeneity. The key manufacturing difference between the two groups of formulations lay in the method of loading the Degarelix into the process. For the 010 series the Degarelix was loaded in DMSO solution whereas for the 015 series (formulations 015A and 015E) the Degarelix was loaded dry with the polymer and DMSO was added afterwards.

In Vivo Testing in Pig Model

The pharmacokinetics of formulations of the invention were tested in a pig model. The animals were castrated male domestic pigs of weight about 35 kg. The animals were split into two groups (Groups 1 and 2), with four animals per group.

The test article was Example 21P as shown in Table 1 above (noting "improved analytics", the degarelix load being 35%). Thus, the test article was degarelix in washed formulation 65% 7525DLG1A/5% trehalose/30% degarelix acetate suspended in aqueous or oily vehicle (see below). The dose per animal was 200 mg degarelix, calculated on the free base.

In Group 1, each pig was administered two IM injections of 2.0 ml of formulation suspended in aqueous vehicle (i.e. 2% CMC, 5% mannitol, 0.1% Tween 80). The total volume was 4.0 ml, split into 2 injections of 2 ml.

In Group 2, each pig was administered two IM injections of 2.0 ml of formulation suspended in sesame oil. The total volume was 4.0 ml, split in 2 injections of 2 ml.

The mean degarelix concentration [ng/mL] was measured at time points of 1, 7, 14, 28, 35, 42, 56 and 84 days after injection, and the results are shown in FIG. 5, alongside those for a comparative study (Formulation F).

As can be seen in FIG. 5, intramuscular administration of Formulations of the invention P maintained mean degarelix concentration well above the 8 ng/mL target level [calculated for pigs, as opposed to the 6 ng/mL target level in the rat] for at least 28 days after administration. These very initial studies in this pig model are understood to represent proof of concept that formulations of the invention may be able to provide sustained release for up to three months, especially after IM administration, in a human model.

The invention claimed is:

1. A pharmaceutical formulation comprising a solid matrix of one or more biodegradable polymers and a pharmaceutically active substance or a pharmaceutically acceptable salt thereof,
   wherein the active substance is distributed uniformly within the matrix on a micrometer scale and the active substance is chosen from gonadotropin releasing hormone (GnRH), a GnRH agonist, and a GnRH antagonist,
   wherein the formulation is made by a process comprising the steps of:
   (a) providing in a vessel the biodegradable polymer in solid form, the pharmaceutically active substance or salt thereof in solid form, and optionally an excipient;
   (b) adding a solvent to the vessel which includes the polymer in solid form and the pharmaceutically active substance in solid form;
   (c) adding a fluid which is capable of existing in a supercritical state to the vessel;
   (d) increasing the temperature and pressure in the vessel to convert the fluid to the supercritical state, optionally mixing the polymer, pharmaceutically active substance, and excipient (if present) prior to, during, and/or after conversion of the fluid to the supercritical state;
   (e) decreasing one or both of the temperature and pressure in the vessel to convert the fluid to a sub-critical state; and then increasing one or both of the temperature and pressure in the vessel to return the fluid to the supercritical state; and
   (f) recovering the solid matrix.

2. The pharmaceutical formulation according to claim 1, wherein the pharmaceutically active substance is degarelix.

3. The pharmaceutical formulation according to claim 2, wherein the amount of degarelix in the pharmaceutical formulation is from 5% to 40% by weight of the solid matrix.

4. The pharmaceutical formulation according to claim 1, further comprising one or more excipients.

5. The pharmaceutical formulation according to claim 4, wherein the one or more excipient is distributed homogeneously or substantially homogeneously within the matrix.

6. The pharmaceutical formulation according to claim 4, wherein the one or more excipient is chosen from a sugar, a sugar alcohol, an inorganic salt, and a synthetic polymer.

7. The pharmaceutical formulation according to claim 1, wherein the biodegradable polymer is polyhydroxy acid (PHA).

8. The pharmaceutical formulation according to claim 7, wherein the polyhydroxy acid (PHA) is chosen from poly (lactic acid) (PLA), poly(glycolic acid) (PGA), a copolymer of lactic and glycolic acid (PLGA), a copolymer of lactic and glycolic acid with poly(ethylene glycol), poly(e-caprolactone) (PCL), and poly(3-hydroxybutyrate) (PHB).

9. The pharmaceutical formulation according to claim 8, wherein the biodegradable polymer is a copolymer of lactic and glycolic acid (PLGA).

10. The pharmaceutical formulation according to claim 9, wherein the PLGA has a molar ratio of lactic acid:glycolic acid of from 90:10 to 10:90.

11. The pharmaceutical formulation according to claim 1, wherein the inherent viscosity of the one or more biodegradable polymer is from about 0.1 to about 0.5 dL/g.

12. The pharmaceutical formulation according to claim 1, wherein the solid matrix is in the form of microparticles.

13. The pharmaceutical formulation according to claim 12, wherein the microparticles have mean particle size from about 25 to about 65 μm expressed as the volume mean diameter (VMD).

14. The pharmaceutical formulation according to claim 1, wherein the formulation is in the form of a suspension.

15. The pharmaceutical formulation according to claim 14, wherein the formulation further comprises a pharmaceutically acceptable carrier.

16. The pharmaceutical formulation according to claim 1, wherein the formulation is in a form for intramuscular administration.

17. The pharmaceutical formulation according to claim 1, wherein the fluid added in step (c) is carbon dioxide.

18. The pharmaceutical formulation according to claim 17, wherein the solvent added in step (b) is an aprotic organic solvent.

19. The pharmaceutical formulation according to claim 18, wherein the aprotic organic solvent is chosen from dimethyl sulfoxide (DMSO), acetone, and an alcohol.

20. The pharmaceutical formulation according to claim 19, wherein the solid matrix is washed in water, a $C_1$ to $C_8$ alcohol, or a solution of a $C_1$ to $C_8$ alcohol in water.

21. A method of treating prostate cancer or benign prostate hyperplasia comprising:
administering to a patient in need thereof a pharmaceutical formulation comprising a solid matrix of one or more biodegradable polymers and a pharmaceutically active substance or a pharmaceutically acceptable salt thereof,
wherein the active substance is distributed uniformly within the matrix on a micrometer scale and the active substance is chosen from gonadotropin releasing hormone (GnRH), a GnRH agonist, and a GnRH antagonist
wherein the pharmaceutical formulation is made by a process comprising the steps of:
(a) providing in a vessel the biodegradable polymer in solid form, the degarelix or salt thereof in solid form, and optionally an excipient;
(b) adding a solvent to the vessel which includes the polymer in solid form and the degarelix in solid form;
(c) adding a fluid which is capable of existing in the supercritical state to the vessel;
(d) increasing the temperature and pressure in the vessel to convert the fluid to the supercritical state, optionally mixing the polymer, degarelix and excipient (if present) prior to, during, and/or after conversion of the fluid to the supercritical state;
(e) decreasing one or both of the temperature and pressure in the vessel to convert the fluid to a sub-critical state; and then increasing one or both of the temperature and pressure in the vessel to return the fluid to the supercritical state; and
(f) recovering the solid matrix.

22. The pharmaceutical formulation according to claim 1, further comprising after step (e), repeating step (e) one or more times.

23. The pharmaceutical formulation according to claim 1, further comprising after step (f), washing the solid matrix.

24. The pharmaceutical formulation according to claim 1, wherein the pharmaceutically active substance is triptorelin.

25. The pharmaceutical formulation according to claim 21, further comprising after step (e), repeating step (e) one or more times.

26. The pharmaceutical formulation according to claim 21, further comprising after step (f), washing the solid matrix.

27. A method of making a pharmaceutical formulation comprising an active substance or pharmaceutically acceptable salt thereof is distributed uniformly within a matrix on a micrometer scale, the method comprising:
(a) providing in a vessel a biodegradable polymer in solid form, the active substance or salt thereof in solid form, and optionally an excipient;
(b) adding a solvent to the vessel which includes the polymer in solid form and the active substance or salt thereof in solid form;
(c) adding a fluid which is capable of existing in the supercritical state to the vessel;
(d) increasing the temperature and pressure in the vessel to convert the fluid to the supercritical state, optionally mixing the polymer, the active substance or salt thereof and excipient (if present) prior to, during, and/or after conversion of the fluid to the supercritical state;
(e) decreasing one or both of the temperature and pressure in the vessel to convert the fluid to a sub-critical state; and then increasing one or both of the temperature and pressure in the vessel to return the fluid to the supercritical state; and
(f) recovering the solid matrix.

* * * * *